United States Patent
Shenoy

(10) Patent No.: US 8,657,838 B2
(45) Date of Patent: Feb. 25, 2014

(54) VASCULAR GRAFT WITH LATERAL OPENING

(75) Inventor: Surendra Shenoy, Olivette, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 13/106,738

(22) Filed: May 12, 2011

(65) Prior Publication Data
US 2011/0282432 A1   Nov. 17, 2011

Related U.S. Application Data

(60) Provisional application No. 61/333,912, filed on May 12, 2010.

(51) Int. Cl.
*A61B 17/08* (2006.01)
*A61F 2/06* (2013.01)

(52) U.S. Cl.
USPC ........................................ 606/153; 623/1.15

(58) Field of Classification Search
USPC ............. 632/1.15, 1.13, 1.53, 1.3, 1.44, 1.22;
606/153, 139; 623/1.35, 1.37, 1.15, 623/1.13, 1.53, 1.3, 1.44, 1.22
See application file for complete search history.

(56) References Cited

U.S. PATENT DOCUMENTS

| | | | |
|---|---|---|---|
| 6,497,710 B2 | 12/2002 | Yencho et al. | |
| 6,585,760 B1 | 7/2003 | Fogarty | |
| 6,609,014 B1 | 8/2003 | Allison et al. | |
| 6,626,920 B2 | 9/2003 | Whayne | |
| 6,652,543 B2 * | 11/2003 | Spence et al. | 606/153 |
| 6,666,884 B1 * | 12/2003 | Webster | 623/1.35 |
| 7,063,712 B2 | 6/2006 | Vargas et al. | |
| 7,892,246 B2 | 2/2011 | Akin et al. | |
| 7,892,247 B2 | 2/2011 | Conston et al. | |
| 2004/0073282 A1 * | 4/2004 | Stanish | 623/1.3 |

OTHER PUBLICATIONS

Gagne et al., "The effect of a venous anastomosis Tyrell vein collar on the primary patency of arteriovenous grafts in patients undergoing hemodialysis", 2000, J. Vasc Surg, pp. 1149-1154, vol. 32.
Lemson et al., "Effects of a venous cuff at the venous anastomosis of polytetrafluoroethylene grafts for hemodialysis vascular access", 2000, J. Vasc Surg, pp. 1155-1163, vol. 32.
Scott et al., "Conduits for Hemodialysis Access", 2007, Semin Vasc Surg, pp. 158-163, vol. 20.
Shenoy, "Innnovative Surgical Approaches to Maximize Arteriovenous Fistula Creation", 2007, Semin Vasc Surg, pp. 141-147, vol. 20.

* cited by examiner

*Primary Examiner* — Gregory Anderson
*Assistant Examiner* — Christina Lauer
(74) *Attorney, Agent, or Firm* — Armstrong Teasdale LLP

(57) ABSTRACT

A vascular graft includes a flexible conduit including a sidewall defining a cavity extending between a first end and a second end. The first end includes an opening that is oriented substantially perpendicular to a centerline axis of the conduit. The second end includes a end wall and a tapered portion extending from the sidewall to the end wall such that the cavity includes a first diameter defined at the first end and a second diameter defined at the second end that is smaller than the first diameter. A lateral opening extends through the sidewall and is oriented substantially parallel to the centerline axis. The lateral opening positioned near the second end and is sized to provide flow communication between the cavity and a blood vessel.

19 Claims, 4 Drawing Sheets

PRIOR ART

VASCULAR GRAFT WITH LATERAL OPENING

CROSS REFERENCE TO RELATED APPLICATIONS

This application claims the priority of U.S. Provisional Patent Application Ser. No. 61/333,912, filed May 12, 2010, which is hereby incorporated by reference in its entirety.

BACKGROUND

Aspects of the disclosure relate generally to vascular grafts and, more particularly, to a vascular graft that facilitates straight onlay coupling to a blood vessel.

Vascular grafts are used to perform anastomosis, the joining of blood vessels (e.g., an artery and a vein). For example, an arteriovenous graft (AVG) extends from an artery to a vein.

Known vascular grafts terminate at both ends in an open cross section, which can be sutured to a wall of a blood vessel such that the graft extends from the blood vessel at an angle determined by how the cross section is cut. In many cases, a vascular graft is oriented approximately perpendicular to the blood vessel. Known vascular grafts are susceptible to the development of stenosis, or narrowing, near and downstream of the anastomosis. Stenosis may be especially pronounced in a patient with end stage renal disease (ESRD), in whom an AVG is used to provide vascular access for hemodialysis. In this context, stenosis may be referred to as venous neointimal hyperplasia (VNH) and can ultimately lead to a failure of the graft.

SUMMARY

In one aspect, a vascular graft is provided. The vascular graft includes a flexible conduit including a sidewall defining a cavity extending between a first end and a second end. The first end includes an opening that is oriented substantially perpendicular to a centerline axis of the conduit. The second end includes a end wall and a tapered portion extending from the sidewall to the end wall such that the cavity includes a first diameter defined at the first end and a second diameter defined at the second end that is smaller than the first diameter. A lateral opening extends through the sidewall and is oriented substantially parallel to the centerline axis. The lateral opening positioned near the second end and is sized to provide flow communication between the cavity and a blood vessel.

In another aspect, a vascular graft system is provided. The vascular graft system includes a first flexible conduit and a second flexible conduit having a sealed vessel end and a coupling end. The coupling end comprises a cross sectional aperture. A connector is configured to couple the coupling end of the first flexible conduit to the coupling end of the second flexible conduit, wherein the first flexible graft and the second flexible graft define a first inside diameter. The connector comprises a cylinder having an outside diameter substantially equal to the inside diameter of the first and second flexible conduits.

DETAILED DESCRIPTION

The term vascular graft generally describes a flexible, tubular conduit used in various vascular surgery procedures as a bridge between two blood vessels (e.g., an artery and a vein). However, embodiments described herein may be used with any fluid vessels. A vascular graft may be composed of synthetic materials, such as expanded polytetrafluroethele (ePTFE), polyurethane urea and/or derivatives thereof, polyethylene terephthalate (PET), and/or silicone. Alternatively, or in addition, a vascular graft may be composed of a biological material, such as bovine carotid artery and/or bovine mesenteric veins.

A vascular graft may be used to join an artery to a vein, in which case the vascular graft may be referred to as an arteriovenous graft (AVG). Existing vascular grafts, including AVGs, are susceptible to venous neointimal hyperplasia (VNH).

Another method of creating dialysis access in end stage renal disease (ESRD) patients is an arteriovenous fistula (AVF). In this method, no graft material is used. Instead the native vein (the patient's own vein) is anastomosed (joined) to the artery to create dialysis access. AVFs are susceptible to the development of narrowing beyond the anastomotic site in the outflow vein. This narrowing in an AVF is termed juxta anastomotic stenosis (JAS).

Stenosis may especially be evident in the outflow vein of an AVF or in the outflow vein just beyond the graft vein anastomosis in an AVG.

A significant amount of research has been performed with respect to stenosis in AVGs and AVFs. Some researchers have focused on the tissue responses that ultimately precipitate the stenosis (narrowing) leading to failure of the AVG or AVF. Based on this, many treatment options directed against some of the targets in this tissue response have been tried. Other researchers have tried different graft materials and changes in the design of graft material to prevent the problem. None of the existing materials, designs, or techniques has shown any substantial benefit in reducing the problem of stenosis.

Figure 1:
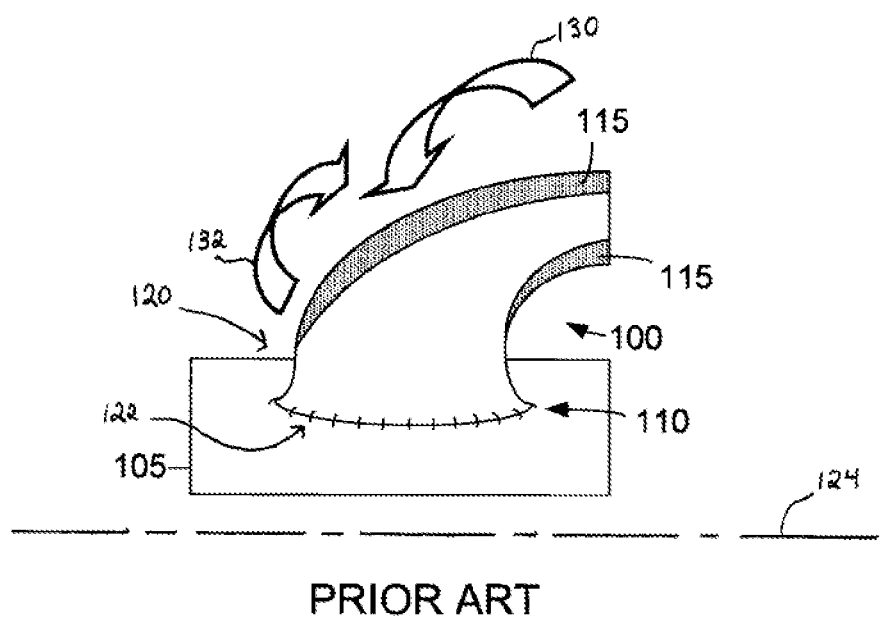
FIG. 1 is an illustration of a known vascular graft extending perpendicularly from a blood vessel.

FIG. 1 is an illustration of a known vascular graft 100 extending perpendicularly from a blood vessel 105. At least some known vascular grafts 100 include a first portion 120 having an open end 122 that is coupled to blood vessel 105 such that first portion 120 is oriented perpendicularly to a flow centerline axis 124 of blood vessel 105, which alters the vein wall configuration at the site 110 of the anastomosis, making it more susceptible to injury produced by the stretch due to increase in the blood flow.

For example, considering the anatomy of an artery and a vein near a wrist or an elbow (where an AV fistula may be positioned), the artery and the vein are situated in two different planes. Current techniques of end-to-side, or perpendicular, anastomosis necessitate the vein to be moved side to side, up and down, and from a vertical axis of an open conduit end to a horizontal axis. In other words, the graft 100 may move with three degrees of freedom with respect to the blood vessel 105. This movement produces a torque, represented by arrows 130 and 132, in the vein wall and/or increases shear stress, making an area 115 of vein wall susceptible to flow injury.

The problem of stenosis development may indicate an inflammatory response of the tissue with altered configuration produced by increased flow caused by the anastomosis. Moreover, the anastomotic configuration resulting from the currently available graft designs combined with the hemodynamic changes resulting from them may be responsible for the development of VNH.

Embodiments described herein facilitate anastomosis via a straight onlay technique ("SLOT"), which alters the configuration shown in FIG. 1. The SLOT technique is operable to reduce the torque on the blood vessel present in the standard technique by reducing one movement of the blood vessel.

Figure 2:
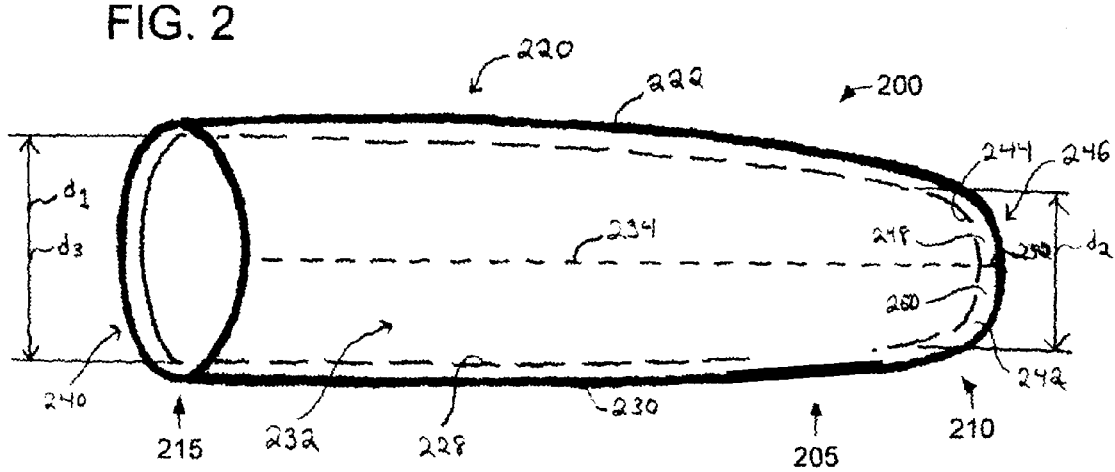
FIG. 2 is an illustration of an exemplary vascular graft with a lateral opening at a blunt end.

FIG. 2 is an illustration of an exemplary vascular graft 200. In the exemplary embodiment, vascular graft 200 includes a flexible conduit 220 having a sidewall 222 that extends between a first end 215 and an opposite second end 210. Sidewall 222 includes a radially inner surface 228 and a radially outer surface 230. Radially inner surface 228 defines a substantially cylindrical cavity 232 extending along a centerline axis 234 between first and second ends 215, 210. In the exemplary embodiment, inner surface 228 has a first diameter $d_1$ defined at first end 215 and a second diameter $d_2$ defined at second end 210. In the exemplary embodiment, second diameter $d_2$ is smaller than first diameter $d_1$. Alternatively, second diameter $d_2$ may be equal to, or larger than, first diameter $d_1$.

In the exemplary embodiment, vascular graft 200 includes a lateral opening or aperture 205 extending through sidewall 222 and positioned closer to second end 210 than first end 215. Lateral opening 205 is sized and shaped to provide flow communication between cavity 232 and blood vessel 105 (shown in FIGS. 6-8). Lateral opening 205 may be round (e.g., circular, ovular, or elliptical) or any other shape suitable for use with the methods described herein. In the exemplary embodiment, vascular graft 200 may be attached to blood vessel 105 such that lateral opening 205 provides flow communication between vascular graft 200 and blood vessel 105. Vascular graft 200 is configured to be coupled (e.g., sutured, clipped, and/or stapled) to blood vessel 105. In the exemplary embodiment, lateral opening 205 is oriented with respect to centerline axis 234 such that second end 210 is oriented substantially tangentially to an outer surface 236 of blood vessel 105. Blood vessel 105 includes an opening 238 extending through outer surface 236. Vascular graft 200 is coupled to blood vessel 105 such that lateral opening 205 is in flow communication with blood vessel opening 238 to enable a flow of fluid to be channeled between vascular graft 200 and blood vessel 105.

In the exemplary embodiment, vascular graft 200 also includes a cross sectional opening 240, i.e. an aperture, defined at first end 215. Opening 240 is oriented substantially perpendicularly to centerline axis 234. Opening 240 includes a cross-sectional diameter $d_3$ that is approximately equal to first diameter $d_1$. In the exemplary embodiment, second end 210 includes an end wall 242 extending from sidewall 222 such that cavity 232 is enclosed by end wall 242. In one embodiment, end wall 242 includes a continuous inner surface 244 that defines a blunt end 246 of vascular graft 200. Alternatively, end wall 242 includes a first portion 248 and a second portion 250 that is coupled to first portion 248 along a joint 252.

In another embodiment, vascular graft 200 does not include lateral opening 205 and is sealed at blunt end 210. Such an embodiment facilitates creation of a lateral opening 205 suitable for a particular operation by a medical practitioner. For example, a surgeon may create lateral opening 205 with a size, a shape, and a position based on blood vessel characteristics (e.g., size, flow rate, and/or orientation) of a patient.

In the context of an AVG, vascular graft 200 facilitates reducing stress and/or torque applied to the blood vessels and/or vascular graft 200. Moreover, use of vascular graft 200 facilitates improved hemodynamics at the anastomosis, which results in a decrease in stenotic problems.

As opposed to at least some known AVF techniques, where the end of a vein (divided tangentially) is anastomosed to an artery, vascular graft 200 allows the appropriate side (e.g., the back or posterior aspect) of the vein, which is a cylindrical structure, to be coupled to the appropriate side (e.g., the front or anterior aspect) of the artery, which once again is a tubular structure. As described herein, the "appropriate" side of a blood vessel may be understood as the side which faces the other blood vessel when the blood vessels are in their natural configuration. Such a "piggyback" configuration of the vein over the artery facilitates reduced torsional stress, distortion, and/or hemodynamic stress on the vein wall. Further, vascular graft 200 enables installation with a reduced need for mobilization of the vessel during surgery and, consequently, reduced tissue trauma.

Figure 3:
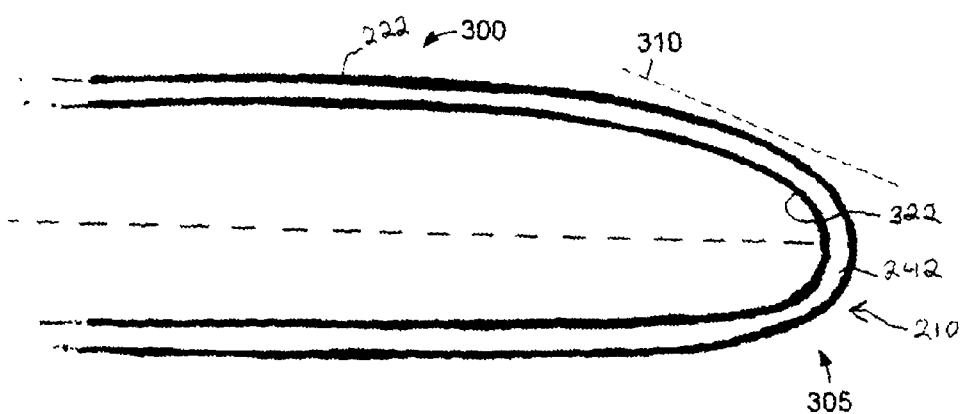
FIG. 3 is an illustration of an exemplary vascular graft with an angulated blunt end.

FIG. 3 is an illustration of an exemplary vascular graft 300 with an angulated blunt end 305. In the exemplary embodiment, second end 210 of vascular graft 300 includes an inner portion 322, as seen from a side perspective, that slopes downward at an angle 310 from sidewall 222 toward end wall 242 such that vascular graft 300 includes a second diameter $d_2$ that is less than first diameter $d_2$. The orientation of inner portion 322 facilitates improved hemodynamics at an anastomosis site.

Figure 6:
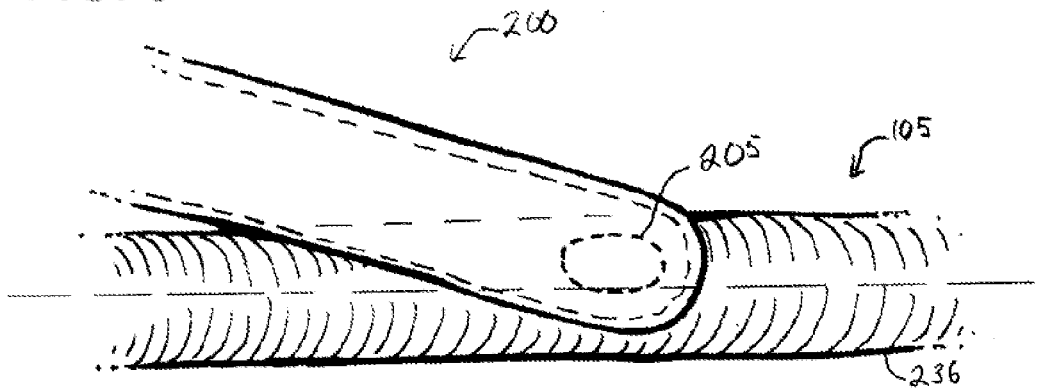
FIG. 6 is an illustration of the vascular graft shown in FIG. 2 coupled to a blood vessel via a lateral opening.
Figure 7:
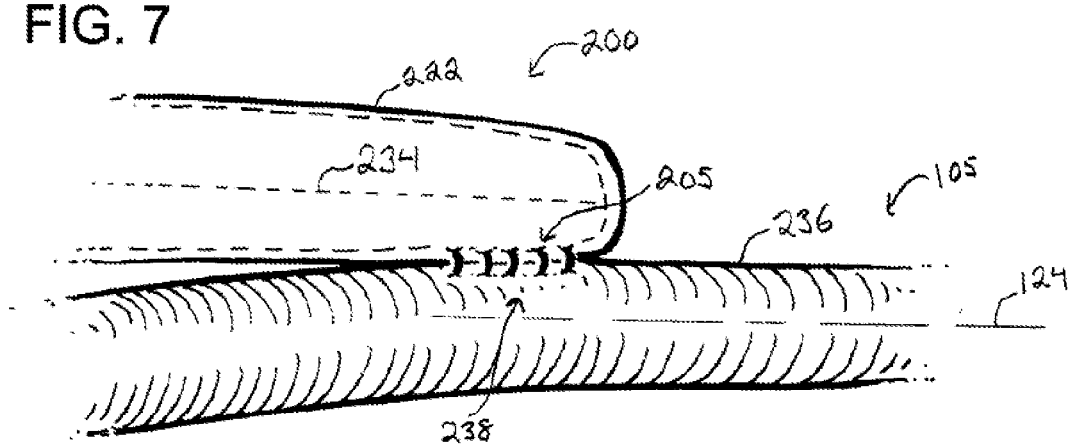
FIG. 7 is a side perspective illustration of the vascular graft and blood vessel shown in FIG. 6.
Figure 8:
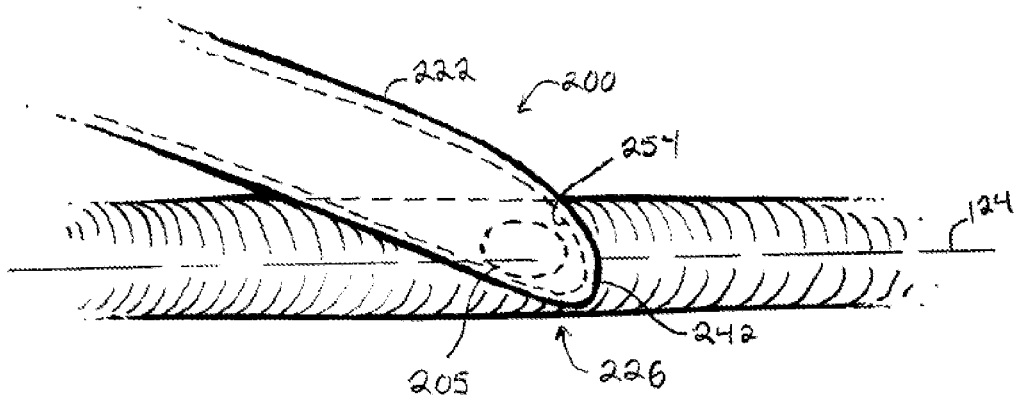
FIG. 8 is an illustration of a vascular graft with a tapered end coupled to a blood vessel via a lateral opening.

FIG. 6 is an illustration of vascular graft 200 shown in FIG. 2 coupled to (e.g., sutured to) blood vessel 105 via lateral opening 205. FIG. 7 is a side perspective illustration of vascular graft 200 and blood vessel 105 shown in FIG. 6. FIG. 8 is an illustration of vascular graft 200 with an angulated second end 210 coupled to blood vessel 105 via lateral opening 205.

As shown in FIGS. 6 and 7, lateral opening 205 of vascular graft 200 is aligned with lateral opening 205 in blood vessel 105 such that centerline axis 234 is obliquely oriented to blood vessel axis 124. Moreover, angulated second end 210 includes an inner portion 254 that is slopped from sidewall 222 to end wall 242 to facilitate providing a smooth or gradual transition for blood flow between blood vessel 105 and vascular graft 200. With vascular graft 200 in a piggyback or SLOT configuration with respect to blood vessel 105, less force and/or torque may be applied to the blood vessel and/or the vascular graft than known configurations wherein the vascular graft extends perpendicularly from the blood vessel.

Figure 4:
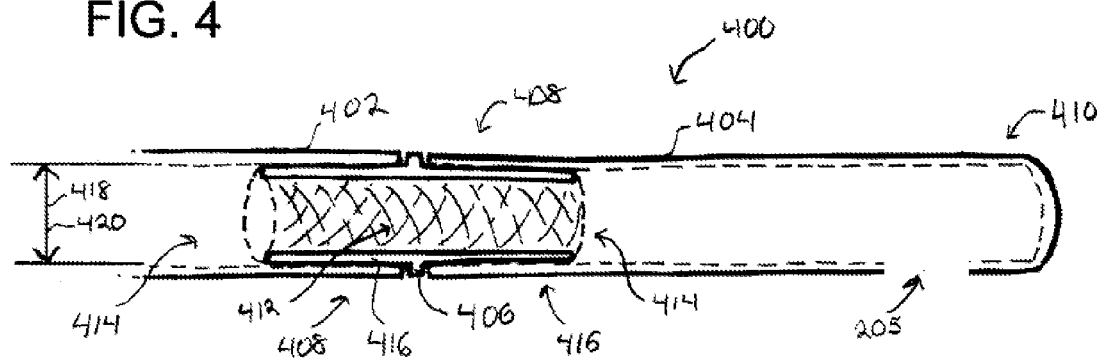
FIG. 4 is an illustration of an exemplary vascular graft system.

FIG. 4 is an illustration of an exemplary vascular graft system 400. As shown in FIG. 4, vascular graft system 400 includes a first vascular graft 402, a second vascular graft 404, and a connector 406 coupled between first and second vascular graft 402 and 404. Each first and second vascular grafts 402 and 404 extend between a coupling end 408 and a sealed end 410, and includes a lateral opening 205 defined near sealed end 410. Each coupling end 408 includes a cross sectional opening 412. Connector 406 engages each cross sectional opening 412 of first and second vascular grafts 402 and 404 such that first vascular graft 402 is in flow communication with second vascular graft 404. In one embodiment, each vascular graft 402 and 404 includes a conduit 414 or lumen including a first end 416 having substantially similar inside diameters 418. Connector 406 includes a cylinder 416 or tube having an outside diameter 420 that is substantially equal to (e.g., within 0.1, 0.2, or 0.5 mm) inside diameters 418 of first and second vascular grafts 402 and 404. In the exemplary embodiment, connector 406 may be rigid or flexible.

In some embodiments, first and second vascular grafts 402 and 404, such as those shown in FIGS. 2 and 3, may be coupled to blood vessel 105 and directly connected to each other via connector 406. In an alternative embodiment, vascular grafts 402 and 404 may be coupled to blood vessels, and each vascular graft may be coupled to an intermediate conduit having a cross sectional opening at each end by a connector.

In the exemplary embodiment, vascular graft system 400 facilitates performing an anastomosis to an outflow vessel and then aligning the outflow graft to avoid any torsional stress on the anastomosis.

Figure 5:
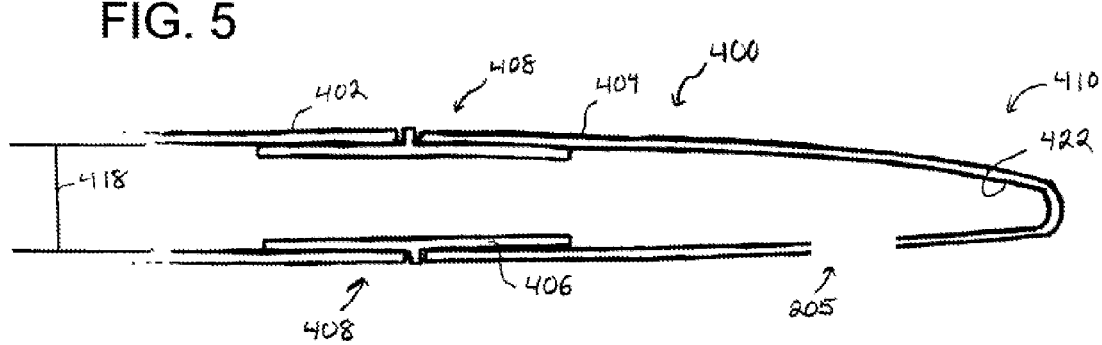
FIG. 5 is an illustration of an exemplary vascular graft system with a tapered blunt end.

FIG. 5 is an illustration of vascular graft system 400 including a second end 410 having a tapered inner portion 422 extending between sidewall 222 and end wall 242. The taper inner portion 422 gradually reduces inside diameter 418 of the vascular grafts 402 and 404 at second end 210. Such an embodiment facilitates modulating blood flow. For example, lateral opening 205 may be positioned at a location corresponding to an inside diameter that will produce a desired blood flow.

When introducing elements of aspects of the invention or embodiments thereof, the articles "a," "an," "the," and "said" are intended to mean that there are one or more of the elements. The terms "comprising," including," and "having" are intended to be inclusive and mean that there may be additional elements other than the listed elements.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A vascular graft comprising:
   a flexible conduit including a sidewall defining a cavity extending between a first end and a second end, the first end including an opening that is oriented substantially perpendicular to a centerline axis of the conduit, the second end including an end wall and a tapered portion extending from the sidewall to the end wall such that the cavity includes a first diameter defined at the first end and a second diameter defined at the second end that is smaller than the first diameter, the end wall including a continuous inner surface that defines a blunt end of the conduit; and
   a lateral opening extending through the sidewall and oriented parallel to the centerline axis, the lateral opening is positioned near the second end and is sized to provide flow communication between the cavity and a blood vessel.

2. The vascular graft set forth in claim 1 wherein the lateral opening is one of circular, ovular and elliptical.

3. The vascular graft set forth in claim 1 wherein the blunt end of the conduit is an angulated blunt end.

4. The vascular graft set forth in claim 3 wherein the conduit tapers inward from the first end towards the second end.

5. The vascular graft set forth in claim 4 wherein a diameter of the conduit at the first end is greater than a diameter of the conduit at the second end.

6. The vascular graft set forth in claim 1 wherein the sidewall is substantially cylindrical.

7. A vascular graft system comprising:
   the vascular graft set forth in claim 1; and
   a connector configured to attach to the first end of the flexible conduit, the opening of the first end being sized and shaped for receiving at least a portion of the connector.

8. The vascular graft system set forth in claim 7 wherein the connector comprises a cylinder having an outside diameter substantially equal to an inside diameter of the conduit at the opening.

9. The vascular graft system set forth in claim 7 wherein the connector is flexible.

10. A method comprising attaching the vascular graft set forth in claim 1 to an outer surface of a blood vessel having an aperture therein such that the lateral opening in the conduit is in fluid communication with the aperture in the blood vessel.

11. The method set forth in claim 10 further comprising aligning the centerline axis of the conduit obliquely with respect to a centerline axis of the blood vessel before attaching the vascular graft to the blood vessel.

12. The method as set forth in claim 11 wherein the vascular graft is attached to the blood vessel in a piggyback configuration.

13. The method as set forth in claim 10 wherein the vascular graft is attached to the blood vessel using at least one of sutures, clips and staples.

14. A vascular graft system comprising:
   a first flexible conduit and a second flexible conduit each having a sealed vessel end and a coupling end, the coupling end comprising a cross sectional aperture, the sealed vessel end of each conduit comprising a continuous inner surface that defines a blunt end of the flexible conduits wherein the second flexible conduit comprises a lateral opening oriented substantially parallel to a centerline axis of the conduit; and
   a connector configured to couple the coupling end of the first flexible conduit to the coupling end of the second flexible conduit, wherein the first flexible conduit and the second flexible conduit define a first inside diameter, and the connector comprises a cylinder having an outside diameter substantially equal to the inside diameter of the first and second flexible conduits.

15. The vascular graft system set forth in claim 14 wherein the lateral opening is positioned closer to the sealed vessel end than the coupling end of the second flexible conduit.

16. The vascular graft system set forth in claim 14 wherein the lateral opening is one of circular, ovular and elliptical.

17. The vascular graft system set forth in claim 14 wherein the blunt end of the second flexible conduit is an angulated blunt end.

18. The vascular graft system set forth in claim 14 wherein the second flexible conduit tapers inward from the coupling end towards the sealed vessel end.

19. The vascular graft system set forth in claim 18 wherein a diameter of the second flexible conduit at the coupling end is greater than a diameter of the second flexible conduit at the sealed vessel end.

\* \* \* \* \*